United States Patent

Borror et al.

[11] 3,975,423
[45] Aug. 17, 1976

[54] ALKYLTHIOALKYL-SUBSTITUTED ALKYLSULFONYLACETONITRILES

[75] Inventors: Alan L. Borror; Richard B. Greenwald, both of Lexington, Mass.

[73] Assignee: Polaroid Corporation, Cambridge, Mass.

[22] Filed: May 8, 1975

[21] Appl. No.: 575,584

[52] U.S. Cl.............................. 260/465.1; 96/60 BF; 96/61 R; 96/29 R; 96/61 M
[51] Int. Cl.$^2$........................................ C07C 121/16
[58] Field of Search................................ 260/465.1

[56] References Cited
UNITED STATES PATENTS

| | | | |
|---|---|---|---|
| 2,978,480 | 4/1961 | Luckenbaugh | 260/465.1 |
| 3,092,542 | 6/1963 | Goodhue et al. | 260/465.1 X |
| 3,142,616 | 7/1964 | Baker et al. | 260/465.1 X |

OTHER PUBLICATIONS

C. A., 49, 1955, Dijkstra et al., 11539-h.

Primary Examiner—Joseph Paul Brust
Attorney, Agent, or Firm—Sybil A. Campbell

[57] ABSTRACT

This application is directed to compounds of the formula

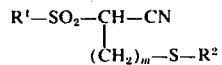

wherein $R^1$ and $R^2$ each represent lower alkyl and m is a whole number 2 to 5, preferably 2 or 3. These compounds are useful as silver halide solvents in photography.

7 Claims, No Drawings

ALKYLTHIOALKYL-SUBSTITUTED ALKYLSULFONYLACETONITRILES

BACKGROUND OF THE INVENTION

1. Field of the Invention

This invention relates to novel chemical compounds useful as silver halide solvents in photography.

2. Description of the Prior Art

Photographic processing composition capable of forming water-soluble complex silver salts are known to be useful in many types of silver halide photography. To obtain a relatively stable image in an exposed and developed photosensitive silver halide emulsion, the silver halide remaining in the unexposed and undeveloped areas of the emulsion should be converted to a soluble silver complex that can be removed by washing or converted to a stable silver complex that will not "print-out" upon prolonged exposure to light. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver halide solvent are then removed from the developed and fixed emulsion by washing with water.

Silver halide solvents also have been employed in monobaths where a single processing composition containing a silver halide developing agent in addition to the silver halide solvent is utilized for both developing and fixing an exposed photosensitive silver halide layer. Silver halide solvents also have been employed in diffusion transfer photograhic processes. Such processes are now well known in the art; see for example, U.S. Pat. Nos. 2,543,181; 2,647,056; 2,983,606; etc. In processes of this type, an exposed silver halide emulsion is treated with a processing composition whereby the exposed silver halide emulsion is developed and a imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes were a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237 of Edwin H. Land.

Various compounds have been employed as silver halide solvents in the photographic processes described above. One of the most commonly employed is sodium thiosulfate. Other silver halide solvents that have been used include thiocyanates, such as potassium and sodium thiocyanate; and cyclic imides, such as barbituric acid and uracil. U.S. Pat. No. 3,769,014 discloses still another class of silver halide solvents, namely, 1,1-bis-sulfonyl alkanes.

The present invention is concerned with novel compounds useful as silver halide solvents in both conventional and diffusion transfer photograhy.

SUMMARY OF THE INVENTION

It is the primary object of the present invention to provide certain chemical compounds as set forth hereinafter.

It is a further object of the present invention to provide novel chemical compounds useful for complexing silver ion, i.e., undeveloped silver halide in photographic processes.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

For a fuller understanding of the nature and objects of the invention reference should be had to the following detailed description.

DETAILED DESCRIPTION OF THE INVENTION

The novel compounds of this invention may be represented by the formula:

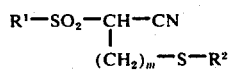

wherein $R^1$ and $R^2$ each represent lower alkyl and $m$ is a whole number 2 to 5, preferably 2 or 3. As used herein, the term lower alkyl is intended to mean alkyl groups containing one to four carbon atoms, for example, methyl, ethyl, propyl, isopropyl, t-butyl and n-butyl.

Specific examples of compounds within the scope of the present invention are as follows:

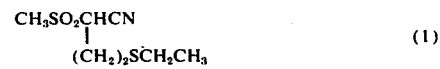   (1)

   (2)

   (3)

   (4)

   (5)

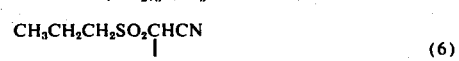   (6)

   (7)

Compounds of the foregoing description are conveniently prepared from the non-S-substituted compounds, i.e., the unsubstituted parent sulfonyl-cyano alkane by reacting with the choro-substituted derivative of the selected $R^2$—S—$(CH_2)_m$—group, viz., $R^2$—

S—$(CH_2)_m$—Cl. The non-S-substituted compounds may be synthesized, for example, according to the procedure reported by R. Dijkstra et al., Chem. Abstr., 49:1153 9h (1955), by reacting a sodium alkylmercaptide ($R^1SNa$) with a chlorosubstituted acetonitrile (e.g., $ClCH_2CN$) to yield the corresponding thio-nitrile ($R^1SCH_2CN$) which is treated with an oxidizing agent, such as, hydrogen perioxide to give the product sulfonyl-cyano alkane ($R^1SO_2CH_2CN$).

The following examples are given to further illustrate the present invention and are not intended to limit the scope thereof.

EXAMPLE 1

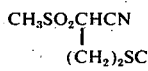

Methylsulfonylacetonitrile ($CH_3SO_2CH_2CN$) (6.0 g., 0.05 mole) in about 0 mls. of N,N-dimethylformamide was added dropwise with stirring to a slurry of sodium hydride (57% by weight dispersion in mineral oil: 2.1 g., 0.05 mole) in 20 mls of N,N-dimethylformamide. The temperature of the mixture rose to about 50°C. accompanied by the vigorous evolution of $H_2$. The mixture was heated to maintain a temperature of about 50°C. for 20 minutes, cooled to about 35°C.; and the chloroethylmethylchloride (5.5 g., 0.05 mole) in about 10 mls. of N,N-dimethylformamide was added dropwise. No immediate reaction occurred. The reaction mixture was heated at 75°–80°C. for 3 hours and cooled followed by the careful addition of water and then ethyl ether. The organic layer was separated leaving the basic aqueous layer which was made acidic with 10% HCl and extracted twice with ethylacetate. After washing with water, the combined ethylacetate extracts were washed with water, dried over magnesium sulfate and evaporated in vacuo to leave 7.8 g. of a reddish oil. Distillation gave 4.1 g. of the title compound as a colorless oil, boiling range 165°–175°C/1mm.

EXAMPLE 2

Preparation of the compound having the formula

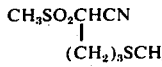

The procedure of Example 1 was repeated except that 3-chloropropylmethylsulfide was reacted with the methylsulfonylacetonitrile ($CH_3SO_2CH_2CN$) and the oil (boiling range 160°–180°C.) obtained upon distillation was triturated with petroleum ether which was decanted leaving 2.8 g. of the title compound.

As noted above, the compounds of the present invention are broadly useful in a variety of photographic processes of the type in which water-soluble silver complexes are formed from the unreduced silver halide of a photoexposed and at least partially developed silver halide stratum including both conventional and diffusion transfer photographic processes. The photographic use of these compounds as silver halide solvents in photographic processes forms the subject matter of copending U.S. Pat. application Ser. No. 575,585 of Alan L. Borror and Richard B. Greenwald filed concurrently herewith. For convenience, the specification of said application is specifically incorporated herein.

To illustrate the utility of the above-defined compounds as photographic silver halide solvents, a photosensitive silver halide emulsion on a support was exposed to a step wedge and processed by spreading a layer of processing composition approximately 1.2 mils. thick between the exposed emulsion and a superposed image-receiving element comprising a layer of regenerated cellulose containing colloidal palladium sulfide carried on a transparent support. The processing composition was prepared by adding the compound of formula 4 in a concentration of 5% by weight to the following formulation:

| | |
|---|---|
| Water | 814.0 g. |
| Potassium hydroxide (Aqueous 50% w/w solution) | 348.0 g. |
| Hydroxyethyl cellulose | 35.0 g. |
| Zinc acetate | 15.0 g. |
| Triethanolamine | 5.6 g. |
| Bis-N,N-methoxyethyl hydroxylamine | 50.0 g. |

After an imbibition period of approximately one minute, the developed silver halide emulsion was separated from the image-receiving element, and the maximum and minimum transmission densities were measured for the positive image. The maximum density obtained was 2.36 and the minimum density was 1.76.

In comparison, methylsulfonylacetonitriles substituted with -S-alkyl, i.e., where the sulfur atom is bonded directly to the carbon atom separating the sulfonyl and cyano groups do not function as photographic silver halide solvents. For example, the compound,

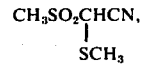

disclosed in aforementioned reference of R. Dijkstra et al. did not exibit silver solvent activity when employed in the above-described photographic procedure, i.e., no transfer silver density was obtained.

Since certain changes may be made in the above compositions and processes without departing from the scope of the invention herein involved, it is intended that all matter contained in the above description should be interpreted as illustrative and not in a limiting sense.

What is claimed is:

1. A compound of the formula

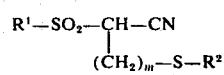

wherein $R^1$ and $R^2$ each represent lower alkyl containing 1 to 4 carbon atoms and $m$ is a whole number 2 to 5.

2. A compound as defined in claim 1 wherein $m$ is 2.
3. A compound as defined in claim 1 wherein $m$ is 3.
4. A compound as defined in claim 1 wherein $R^1$ is methyl.
5. A compound as defined in claim 1 wherein $R^2$ is methyl.
6. The compound having the formula

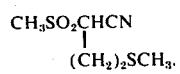
7. The compound having the formula
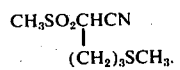
* * * * *